United States Patent [19]

Menard et al.

[11] Patent Number: 4,793,280

[45] Date of Patent: Dec. 27, 1988

[54] METHOD AND APPARATUS FOR PROVIDING POWDER INTO FIBROUS WEB STRUCTURES

[75] Inventors: Michael J. Menard, Doylestown, Pa.; Thomas J. Helmstetter, Sr., Piscataway, N.J.; David E. Johnson, Newton, Pa.

[73] Assignee: Personal Products Company, Milltown, N.J.

[21] Appl. No.: 72,947

[22] Filed: Jul. 13, 1987

Related U.S. Application Data

[62] Division of Ser. No. 897,171, Aug. 15, 1986, Pat. No. 4,699,808.

[51] Int. Cl.$^4$ .............................................. B05B 13/02
[52] U.S. Cl. ........................................ 118/44; 118/72; 118/120; 118/308; 118/312
[58] Field of Search ............... 118/308, 312, 72, 44, 118/32, 120; 156/283

[56] References Cited

U.S. PATENT DOCUMENTS

| 278,212 | 5/1883 | Birge | 118/308 X |
| 619,617 | 2/1899 | Reichenbach | 118/32 X |
| 1,841,539 | 1/1932 | Kleinschmit | 118/32 X |
| 2,723,937 | 11/1955 | Rice | 156/283 X |
| 3,211,600 | 10/1965 | Motycka | 156/283 X |
| 3,908,591 | 9/1975 | Hall | 118/308 |
| 4,415,610 | 11/1983 | Choinski | 118/32 X |

*Primary Examiner*—Shrive Beck

[57] ABSTRACT

A method and apparatus for incorporating a powder into a continuous fibrous web containing multiple corrugations. In the method, a fibrous web provided with multiple parallel corrugations is continuously passed over a curved surface having an arc with a radius to web thickness ratio of 0.5-3 and the corrugations are opened at their upper side, while any bonded fibers connecting adjacent corrugations together are broken apart. A powder having 50-1000 micron particle size is deposited by gravity into the opened spaces between adjacent corrugations of the web. The deposited powder is then compacted into the fibrous corrugated web by rubbing with a pad moved in an oscillating motion generally perpendicular to the corrugations. The powder filled web is bent in the opposite direction around a roller to break the fibers between the corrugations on the opposite side of the web. The second roller can be made vertically movable so as to convert the web continuous forward motion to an intermittent forward motion.

3 Claims, 4 Drawing Sheets

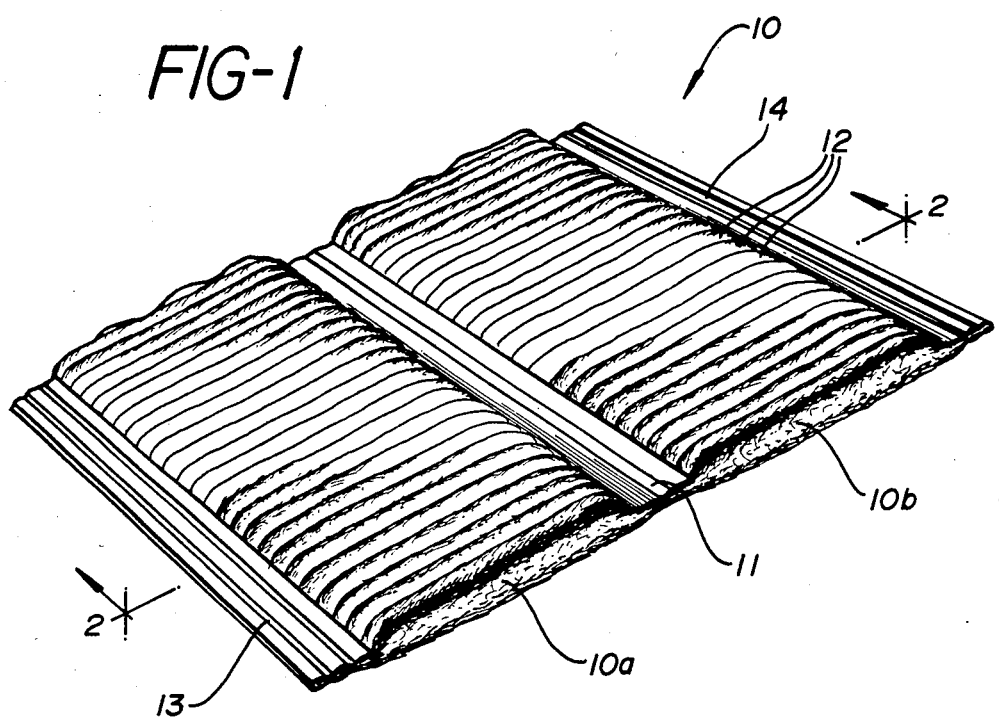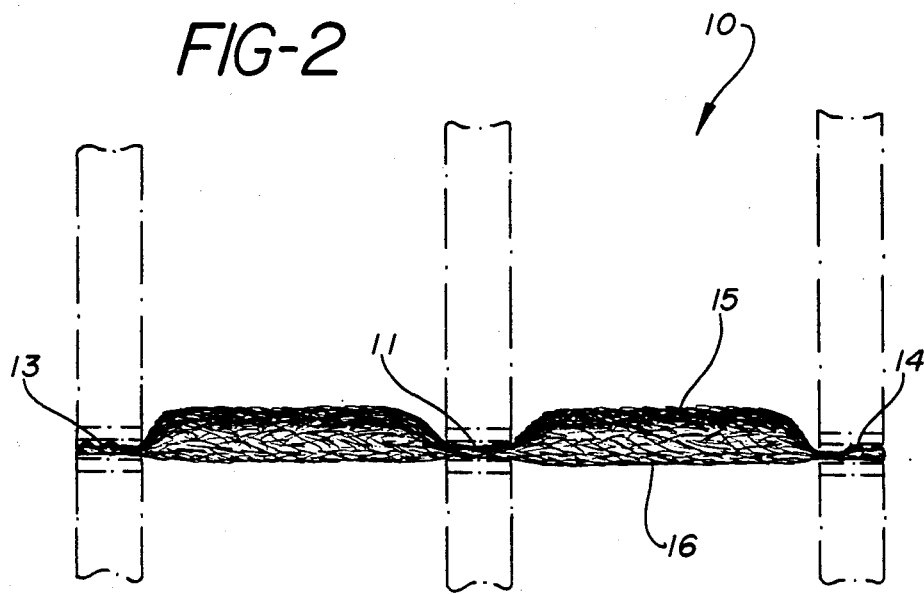

METHOD AND APPARATUS FOR PROVIDING POWDER INTO FIBROUS WEB STRUCTURES

This is a division of application Ser. No. 897,171, filed Aug. 15, 1986, now U.S. Pat. No. 4,699,808.

This invention relates to providing a powder into fibrous webs, and particularly relates to providing an absorbent powder material into a corrugated fibrous web to provide an absorbent fibrous web structure.

Applying powder materials to fabrics is generally known, such as adding powder sizing or starch materials to fabrics to impart stiffness or adding abrasive particles to fabrics to make polishing cloths. Also, absorbent fibrous products and structures are generally known and have been used in disposable diapers, sanitary napkins, incontinent pads, and the like. It has been found quite desirable to incorporate absorbent powders into such fibrous structures, such as disclosed by U.S. Pat. No. 3,670,371. The present invention provides a new and improved method for providing powders into fibrous web structures, particularly into corrugated fibrous web structures such as those disclosed in U.S. Pat. No. 4,578,070 so as to achieve a uniform high loading of an absorbent powder into the web structure.

SUMMARY OF THE INVENTION

This invention provides a method and apparatus for providing a powder material between and into a continuous fibrous web having multiple corrugations and preferably for providing absorbent powders into such fibrous web materials to provide absorbent fibrous web structures. The method includes: providing a continuous flexible fibrous web preferably having dual layers and multiple parallel corrugations formed therein, the corrugations being oriented transverse to the web length and closed together having spacing of 1.2–6 corrugations per inch of length; passing the corrugated web over a curved surface to open the corrugations on the web upper side, the arc of the curved surface having a radium to web thickness ratio of about 0.5 to about 3. By bending the web, open spaces are created between the corrugations on the web upper side. A powder having a particle size of 50–1000 microns and preferably 100–600 microns is deposited into the opened spaces between the adjacent corrugations so as to achieve a powder/web weight ration of at least about 0.5:1 and preferably a ratio between 1:1 and 10:1. The deposited powder is then compacted into the corrugated fibrous web.

The method steps of the invention includes breaking fiber bonds between the web adjacent corrugations on the upper side, while passing the corrugated web sheet over the curved surface to bend the sheet and open the corrugations. Also to increase the powder concentration or loading in the web, the powder deposited in the web sheet corrugations is compacted and forced into the corrugations by placing a pad against the web corrugations and applying a light pressure of 0.5–10 pound/sq. fit. while oscillating the pad in a direction substantially perpendicular to the corrugations.

The web is preferably passed continuously below the powder depositing orifice. If desired for subsequent processing, the powder-filled web can be passed through a motion changing step in which movement of the web is changed from continuous to intermittent motion steps, prior to subsequent processing steps for the web. Also if desired, the powder-filled web can be inverted to place the powder-filled side downward by passing the web over an inverting step provided by a roll bend oriented to change the direction of motion of the web by about 90° angle.

The present invention also includes an apparatus for providing a powder into a corrugated fibrous web, and comprises means for feeding the fibrous web over a roller to bend the web and open the adjacent corrugations; means for feeding the power continuously onto the corrugated web while the adjacent corrugations are opened and for substantially filling the corrugations with the powder; and means for compacting the powder into the web corrugations, whereby the corrugations are substantially completely filled with the powder. A vertically-movable roller device is provided under which the powder-filled web is passed for changing continuous motion of the web to an intermittent motion as needed for subsequent processing steps. Also a roll bend is provided oriented at about 45° angle to the direction of motion of the web for inverting the web.

The method and apparatus of the present invention provides the advantages that powder materials such as an absorbent powder is conveniently and effectively provided into a fibrous corrugated web in amount at least about 50% and usually 100–500% based on the web weight. Then if the web is later inverted, the powder is substantially retained in the web and does not fall out during any subsequent processing steps performed on the web.

BRIEF DESCRIPTION OF DRAWINGS

The invention will be further described by reference to the following drawings, in which:

FIG. 1 shows a perspective view of a fibrous web having multiple transverse corrugations and longitudinal embossed portions provided in the web;

FIG. 2 shows a cross-sectional view of the fibrous web material taken at section 2—2 of FIG. 1;

DESCRIPTION OF INVENTION

Figure 3:
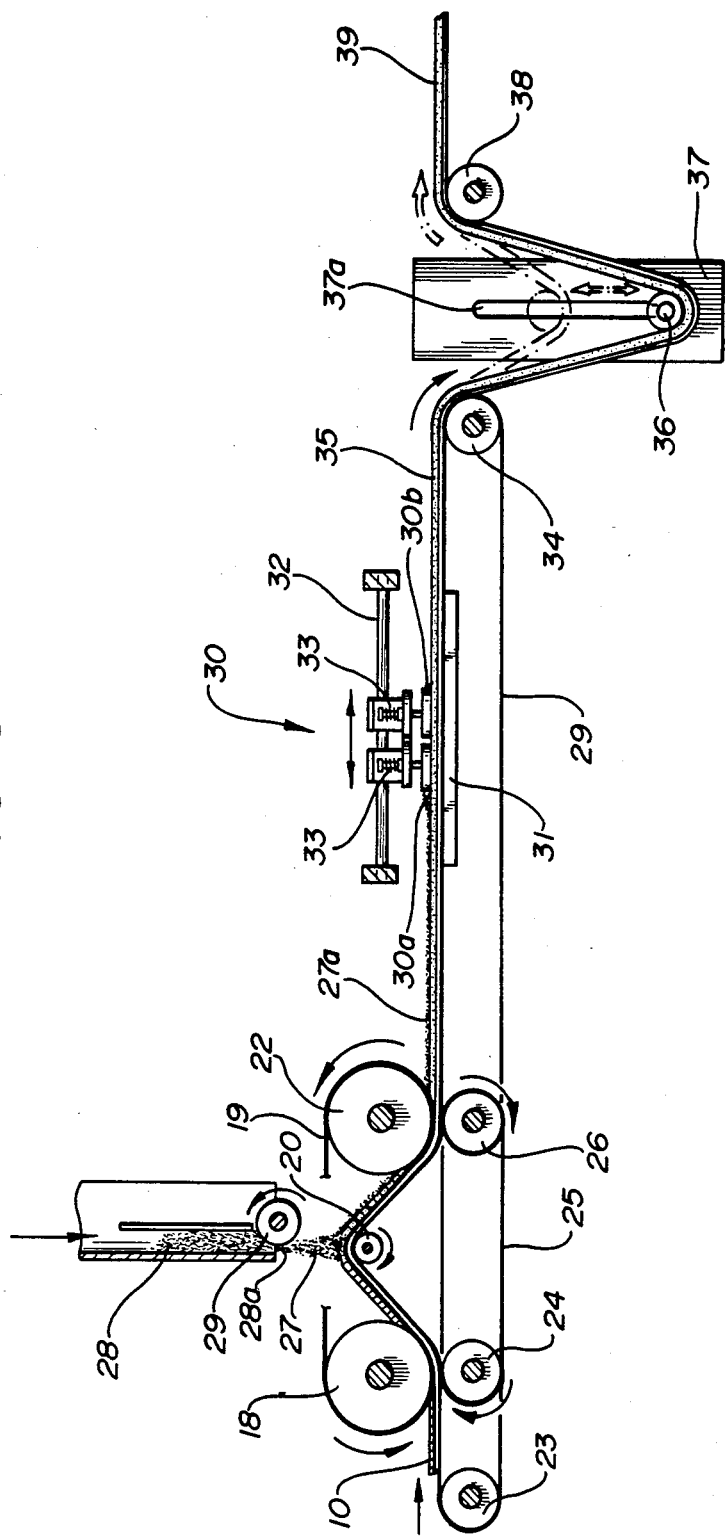
FIG. 3 shows a schematic elevation view of a corrugated fibrous web having a powder material deposited and compacted into the corrugations of the web, followed by a motion changing step for the web.

As generally shown by FIG. 1, a continuous fibrous web 10 is provided having multiple parallel corrugations 12 arranged in two parallel portions 10a and 10b of the web, which portions are separated by a central embossed band portion 11 of the web. The fibrous web 10 also has embossed bands at 13 and 14 located along each edge of the web. The web 10 is preferably made in two layers 15 and 16 of fibrous web material as generally shown by FIG. 2, with the upper layer 15 having a less open structure and smaller void volume than the lower layer 16.

As generally shown by FIG. 3, the fibrous web 10 is continuously fed from a suitable supply source at 17 under a guide roller 18 and over a bending roller 20, and then under a second guide roller 22. The guide rollers 18, 20 and 22 are connected together by a belt 19, which contacts the embossed strips 11, 13 and 14 of the corrugated web 10. Also provided beneath the embossed strips 11, 13 and 14 of web 10 are rollers 23, 24 and 26, which are connected together by a plurality of parallel belts 25. The belts 19 and 25 are positioned on opposite sides of the compacted embossed portions 11, 13 and 14 of the web, so that these belts serve to grip the web 10 and draw it through the powder filling steps at surface speed of 20–60 ft/minute as described hereinbelow. The rollers 18, 20, 22, 23, 24 and 26 are each driven by supporting rotary shafts at substantially the same surface speed.

While the web 10 is passed over the bending roller 20, the upper ends of the web corrugations 12 are opened and a portion of the bonded fibers connecting the adjacent corrugations together are broken. A powder material 27 is deposited by gravity from a dispenser 28 into spaces 12a between the opened corrugations in a quantity sufficient to substantially fill the spaces between the corrugations with the powder, as is generally shown by FIG. 3. From the dispenser 28, the powder is metered through a variable width slot 28a by a rotating knurled roller 29 used in combination with a counter rotating brush used in combination with a counter rotating brush to provide a powder/web weight ratio of at least about 0.5/1 and preferably a weight ratio between 1/1 and 10/1. Although the powder can have a wide particle size range of 50–1000 microns, a powder particle size of 100–600 microns is usually preferred.

Figure 4:
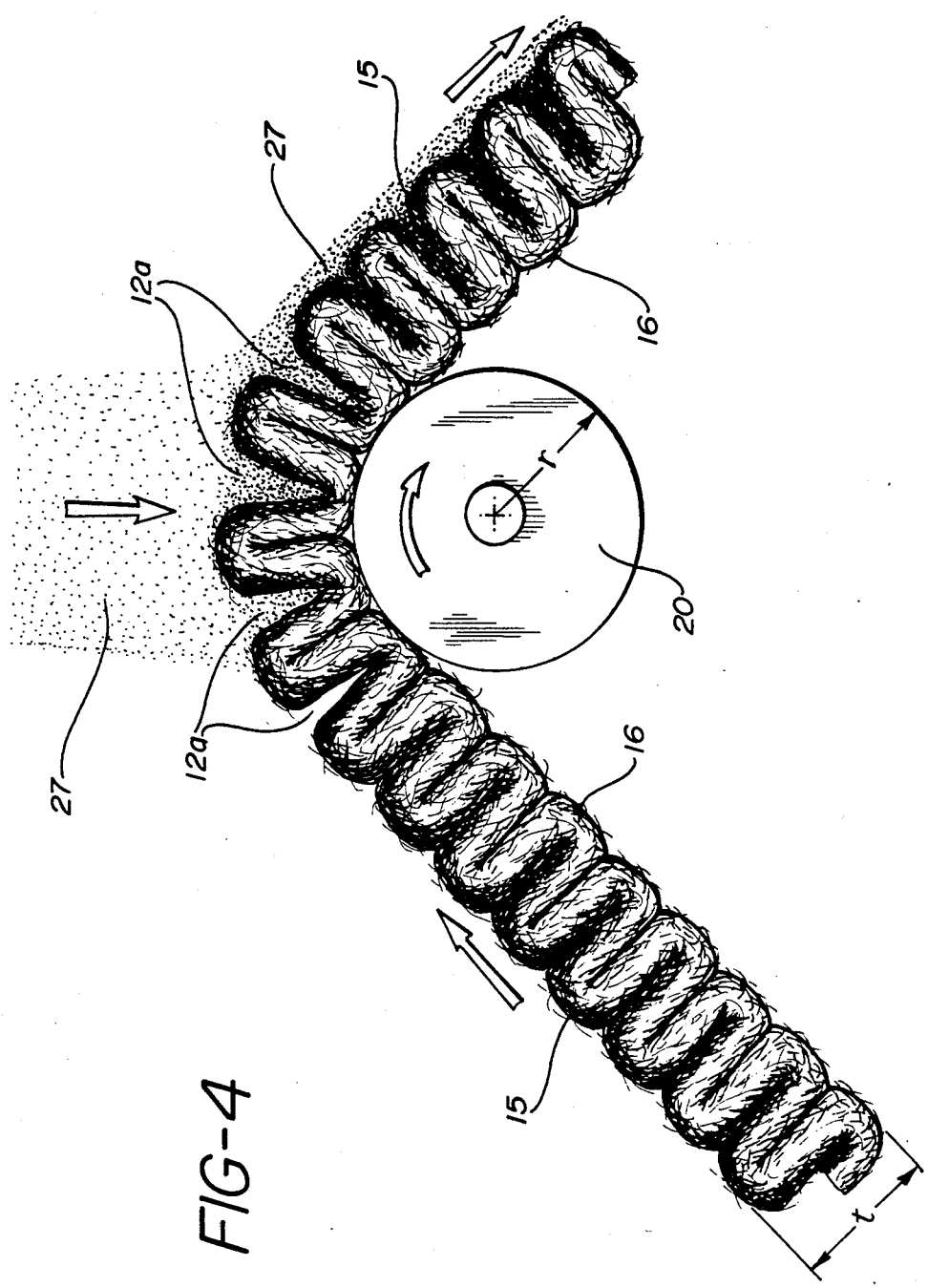
FIG. 4 shows a cross-sectional view of the web corrugations being opened and filled with a powder material.

This powder-filling step for the corrugated web 10 is shown in greater detail by FIG. 4. The corrugated fibrous web 10 is passed over roller 20 so that the spaces 12a between adjacent corrugations 12 are opened to permit their being substantially filled by the powder 27. To provide sufficient opening of the spaces, the radius "r" of roller 20 should have a ratio to thickness "t" of the web within a range of about 0.5–3. Also, the powder particle size relative to the web fiber density is such that substantially all the particles are retained within the upper layer 15 of the web 10. If desired, the powder can be agglomerated by addition of a suitable binder material such as a hydrocarbon liquid or wax to help retain the powder within the web. As the web is passed over roller 20, the spacing of the lower layer 16 of the web 10 is maintained substantially unchanged by the restraining effect of embossed portions 11, 13 and 14 of the web 10.

Referring again to FIG. 3, after the powder-filled web 10 has passed under the second guide roller 22, the web is next contacted on its upper side by at least one rubbing pad 30 which is pressed lightly against the web. The pad 30 is moved in a reciprocating motion parallel with the direction of movement of the web 10 and transverse to the web corrugations 12 by horizontal support rods 32 and a suitable crank mechanism (not shown) at an average surface speed, exceeding the web surface speed, while the pad(s) exert a slight pressure of at least about 0.5 pounds/ft$^2$ and preferably 2–10 lb/ft$^2$ on the powder-filled web. A stationary support plate 31 is provided below the pad and belts to support the pad rubbing pressure on the web.

The pad 30 is preferably provided as two parts 30a and 30b, for which the pressure against the web can be varied separately by springs 33 as desired. This combination of pad reciprocating movement and pressure on the powder on the corrugated web serves to further force the powder 27a into the spaces 12a between the web corrugations 12 and also between the web fibers, so that an increased concentration of powder can be desirably incorporated into the fibrous web 10, and the powder will not fall out when the web is later inverted. After such compacting of the powder, the powder/web weight ratio is at least about 0.5 and is preferably 1.0–10.0. The web 10 is supported during the powder compacting step by a plurality of parallel belts 29 which extend around rollers 24, 26 and 34 and by the support plate 31, as is shown by FIG. 3.

Following such compacting of the powder 27a into the fibrous web 10, the powder-filled web at 35 is passed over guide roller 34 and then under a roller 36, which is arranged to be vertically-movable within dual slots 37a of a guide structure 37 provided at each end of the roller 36. This roller 36 should have a ratio of roller radius to web thickness within a range of about 0.5–3, and also serves to bend the web and break bonded fibers between adjacent corrugations of the web. The vertical movement of the roller 36 aids in converting the continuous forward motion of the web sheet at 35 into an intermittent forward motion for the web at guide roller 38 and beyond as required for subsequent processing steps.

Figure 5:
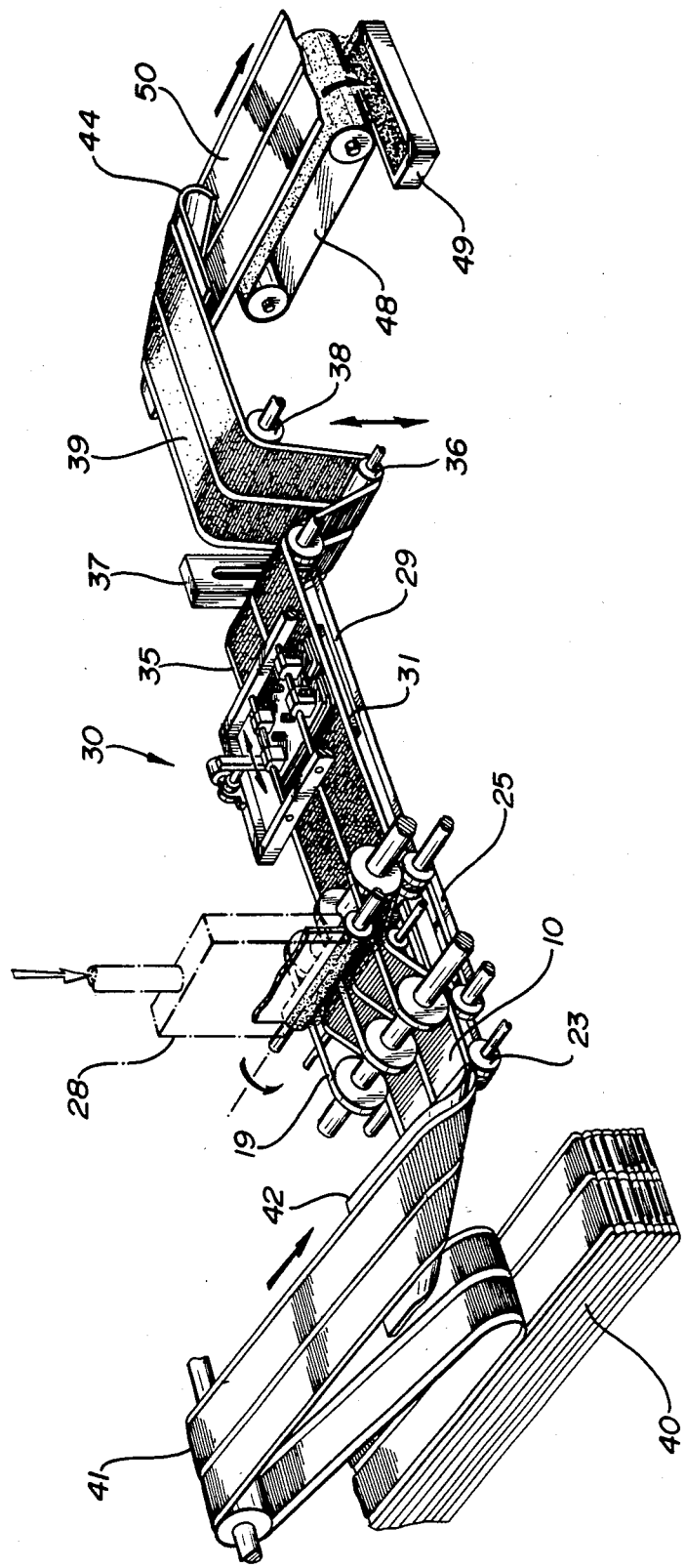
FIG. 5 shows a perspective view of the corrugated fibrous web, including the powder depositing and compacting steps and the motion changing step according to the invention.

FIG. 5 shows a perspective view of the web powder-filling and compacting steps. The web 10 is conveniently provided from a folded stack 40 and passed over a feed roller 41 and a roll bend 42 to the powder-filling step. The powder is deposited from dispenser 28 at the desired rate in combination with the continuous forward motion of the web 10 to provide a powder/web weight ratio between about 1/1 and 10/1 on the web, as was described above. Any powder which may fall onto the embossed portions 11, 13 and 14 of the web 10 is removed by suction nozzles connected to a vacuum system (not shown).

The powder-filled web at 39 is then preferably passed over a stationary inverted roll bend 44, in which the web is inverted while its direction of movement is changed by an angle of about 90°, as generally shown by FIG. 5. Following such web inversion, the powder-filled layer of the web 10 is located on the lower side and any surplus powder 27a not retained within the corrugated web falls out and is recovered, such as by a belt 48 and collection container 49, or by an elongated receptacle provided below the inverted web (not shown). The powder filled inverted web at 50 is then passed on to subsequent processing steps as desired.

The fibrous web usually contains synthetic resilient fibers such as polyester, polyethylene, polypropylene, polyamide fibers, bicomponent fibers, copolymers, and mixtures thereof and the like. In addition, cellulosic fibers such as rayon, wood pulp fibers, acrylic fibers and the like may be used. The web thickness is at least about 0.3 inch and is preferably 0.5–1.5 inches and contains 1.5–5 transverse corrugations per inch. The web overall width is 12–24 inches, and the embossed strip portions of the web are each 0.75–2.0 inches wide.

The powder particle size range is 50–100 microns, and is preferably an absorbent powder having a particle size of 100–500 microns, consisting of a water-insoluble, water-swellable polymeric substance, and may be mixed with 1–10 percent by weight polyethylene glycol to cause agglomeration and suppress dusting of the powder during filling of the web.

This invention will be further described by reference to the following example, which should not be construed as limiting in scope of the invention.

EXAMPLE

A continuous elongated corrugated fibrous web is composed of two superimposed layers of fibrous material and has a flat embossed portion extending along each side and in a middle portion of the web. The corrugated web is gripped on both sides of each embossed portion by a sets of mating belts and is drawn over a bend roller to open the corrugations upper side, while an absorbent powder is deposited by gravity feed into the upper side opened spaces between the adjacent opened corrugations. The fibrous web and powder have characteristics as listed in Table 1 below.

TABLE 1

| Characteristics of Corrugated Fibrous Web and Powder | |
|---|---|
| Web material | polyester fibers |
| Web thickness, inches | 0.75–1.0 |
| Web width, inches | 18–20 |
| Embossed strip width, in. | 1–2 |
| Number of web corrugations per inch | 3.5–4 |
| Ratio of bending roller radius to web thickness | 1.0 |
| Powder composition | Potassium acrylate |
| ——Powder particle size range | 100–400 microns |
| Absorbent powder added to web, weight % of web | 100–150 |

After the powder is deposited in the web upper layer, the web is passed under a rubbing pad oscillating at 30 strokes per minute which exerts a light pressure of 2–3 pounds/ft$^2$ on the powder to force it further into the web corrugations, so as to provide a desired powder/web ratio of about 1.0/1 for the fibrous web structure.

From the above description, it will be apparent that numerous modification and variations may be made to the powder filling steps and apparatus without departing from the scope of the invention, which is defined by the following claims.

We claim:

1. An apparatus for providing a powder material into a corrugated fibrous web, the apparatus comprising:
   (a) web feeding means for continuously feeding a corrugated fibrous web over a roller to open spaces between the web corrugations, said feeding means including dual belts gripping the web;
   (b) means for continuously feeding a powder by gravity onto the web corrugations while the corrugations are opened, so as to substantially fill the spaces between the corrugations with the powder;
   (c) reciprocating pad means for compacting the powder into the web corrugations, whereby the corrugations are substantially completely filled with the powder; and
   (d) a vertically-movable roller under which the powder-filled web is passed for changing continuous forward motion of the web to an intermittent forward motion of the web.

2. The apparatus according to claim 1, including a rollover bend means for inverting the moving powder-filled web.

3. The apparatus according to claim 1, wherein the powder feeding means includes a box oriented transverse to the web and containing a knurled roller located adjacent a variable width slot in the box lower side.

* * * * *